(12) United States Patent
Wallace et al.

(10) Patent No.: US 11,547,295 B2
(45) Date of Patent: Jan. 10, 2023

(54) CLOUD BASED CORNEAL SURFACE DIFFERENCE MAPPING SYSTEM AND METHOD

(71) Applicant: Davco, LLC, Los Angeles, CA (US)

(72) Inventors: David A. Wallace, Los Angeles, CA (US); Stephen D Klyce, Port Washington, NY (US)

(73) Assignee: DAVCO, LLC, Los Angeles, CA (US)

( * ) Notice: Subject to any disclaimer, the term of this patent is extended or adjusted under 35 U.S.C. 154(b) by 5 days.

(21) Appl. No.: 17/204,226

(22) Filed: Mar. 17, 2021

(65) Prior Publication Data

US 2021/0196117 A1 Jul. 1, 2021

Related U.S. Application Data

(63) Continuation of application No. 17/029,390, filed on Sep. 23, 2020, now abandoned.

(Continued)

(51) Int. Cl.
*G16H 10/60* (2018.01)
*G16H 50/70* (2018.01)
(Continued)

(52) U.S. Cl.
CPC .............. *A61B 3/107* (2013.01); *G06F 21/32* (2013.01); *G06F 21/6245* (2013.01);
(Continued)

(58) Field of Classification Search
CPC ........ A61B 3/107; G16H 40/67; G16H 10/60; G16H 50/70; G16H 30/00; G16H 40/63; G06F 21/32; G06F 21/6245
See application file for complete search history.

(56) References Cited

U.S. PATENT DOCUMENTS 5,220,360 A * 6/1993 Verdooner ............... A61B 3/12
351/212
8,517,224 B2 8/2013 Cipriano
(Continued)

FOREIGN PATENT DOCUMENTS

WO WO2002071304 A3 * 9/2002 ............. G16H 15/00

OTHER PUBLICATIONS

International Search Report and Written Opinion of the International Searching Authority, dated Feb. 10, 2021, PCT/US2020/052318, 16 pages.
(Continued)

*Primary Examiner* — Jonathan Durant
*Assistant Examiner* — Anne-Marie K Alderson

(57) ABSTRACT

A method to perform automatic corneal topography or tomography difference mapping includes receiving one or more corneal topography or tomography data files and/or a corneal image for an examined patient from a corneal topography or tomography system; receiving personal identification parameters from captured user personal data communicated from the corneal topography or tomography system; and comparing received patient identification parameters to existing patient identification parameters in a database to identify if there are existing topography or tomography data files for a same patient in the database. The method may further include retrieving a prior topography or tomography data file for the patient from the database; and performing difference mapping by comparing the received topography or tomography data files to the prior topography or tomography data file retrieved from the database to generate a topography or tomography difference map.

12 Claims, 8 Drawing Sheets
(3 of 8 Drawing Sheet(s) Filed in Color)

Related U.S. Application Data

(60) Provisional application No. 62/977,652, filed on Feb. 17, 2020, provisional application No. 62/904,926, filed on Sep. 24, 2019.

(51) Int. Cl.

| | | |
|---|---|---|
| *G16H 40/63* | (2018.01) | |
| *G16H 40/67* | (2018.01) | |
| *G16H 30/00* | (2018.01) | |
| *A61B 3/107* | (2006.01) | |
| *G06F 21/32* | (2013.01) | |
| *G06F 21/62* | (2013.01) | |

(52) U.S. Cl.
CPC ............. *G16H 10/60* (2018.01); *G16H 30/00* (2018.01); *G16H 40/63* (2018.01); *G16H 40/67* (2018.01); *G16H 50/70* (2018.01)

(56) References Cited

U.S. PATENT DOCUMENTS

| | | | |
|---|---|---|---|
| 2004/0128165 A1* | 7/2004 | Block | G16H 10/60 705/2 |
| 2005/0027995 A1* | 2/2005 | Menschik | G16H 40/67 713/193 |
| 2006/0280340 A1* | 12/2006 | Derakhshani | G06K 9/00597 382/117 |
| 2007/0258630 A1 | 11/2007 | Tobin et al. | |
| 2008/0203107 A1* | 8/2008 | Conley | G07F 11/16 221/1 |
| 2008/0312552 A1* | 12/2008 | Zhou | G06T 7/0012 600/558 |
| 2013/0109929 A1* | 5/2013 | Menzel | A61B 90/98 600/301 |
| 2013/0304542 A1* | 11/2013 | Powell | G16H 10/20 705/7.32 |
| 2015/0133901 A1* | 5/2015 | Serdarevic | A61F 9/0079 606/5 |
| 2015/0335474 A1 | 11/2015 | Levis et al. | |
| 2017/0038951 A1* | 2/2017 | Reicher | G06F 16/583 |
| 2017/0042421 A1* | 2/2017 | Wallace | A61B 3/135 |
| 2017/0372029 A1* | 12/2017 | Saliman | G16H 10/60 |
| 2018/0137247 A1* | 5/2018 | Bore | G16H 10/60 |
| 2018/0325605 A1* | 11/2018 | Scherr | A61B 90/96 |

OTHER PUBLICATIONS

Knorz et al. "Topographically-guided laser in situ keatomileusis to treat corneal irregularities." in Ophthalmology, Mar. 1, 2000 Retrieved on Jan. 2021 (Jan. 4, 2021) Cite 2 retrieved from <https:freevis.de/knorz/PIIS0161642000000944.pdf> entire document.

Klyce SD, Oshiga T: Placido-based topography. In Corneal Surgery: Theory, Technique, & Tissue. Part II. Testing and Measuring Corneal Function. 4$^{th}$ edition. FS Brightbill FS, McDonnell PJ, Farjo AA, McGhee CNJ, Serdarevic ON, Mosby Elsevier, New York, NY, 2009, pp. 75-82.

Klyce SD: The Tomey TMS corneal topographer. In: *Corneal Topography in the Wavefront Era*, Chapter 22, Ed by Wang M, Slack, Inc, Thorofare, NJ, 2006, pp. 249-258.

Klyce SD, Espana EM, Waring GO IV. Preoperative Considerations: Corneal Topography. In: *Copeland and Afshari's Principles and Practice of Cornea*. vol. 2, Section 16, Chapter 94. Ed by Copeland Jr RA, Afshari NA. Jaypee Brothers Medical Publishers, Ltd, New Delhi, 2013, pp. 1213-1230.

\* cited by examiner

Example of a difference map obtained with prior art. See text for details.

Identification of very small topographic change through difference mapping. See text for details.

Identification of very small topographic change through difference mapping. See text for details.

CLOUD BASED CORNEAL SURFACE DIFFERENCE MAPPING SYSTEM AND METHOD

RELATED APPLICATIONS

This application claims priority to U.S. provisional patent application Ser. No. 62/904,926, filed Sep. 24, 2019 and U.S. provisional patent application Ser. No. 62/977,652, filed Feb. 17, 2020, the disclosures of which are both hereby incorporated by reference.

BACKGROUND

Corneal topographers measure corneal shape and optical power; they are a key diagnostic tool in many sectors of eye care. Corneal topography instruments measure the anterior surface of the cornea and generate datafiles based on the anterior surface curvature measurements. Corneal tomography systems measure the posterior surface of the cornea and the anterior surface of the cornea and generate datafiles based on the anterior and posterior elevation measurements. While the specification below focuses on discussions of corneal topography, the devices, apparatus and methods described herein in the claimed subject matter apply also to corneal tomography systems. The instruments are commonly used for diverse applications including routine eye examination, evaluating corneal disease states, aiding contact lens fitting, assessing candidacy for cataract and intraocular lens implant surgery, and/or evaluating patients for laser vision correction surgery (LASIK, SMILE, PRK). Current corneal topography equipment consists of sizeable, table-mounted instruments that may interface with dedicated computers to produce color-coded topographic power maps and statistical analyses of the corneal surface that are displayed on a computer monitor, to be evaluated by the eye care practitioner. Some of these systems have an integral display screen, and do not interface with an external computer. Test results can be printed out on a separate printer and image files stored locally, such as on the local computer running the corneal topography device, and/or in local area network ("LAN") locations, and/or in local Electronic Health Record ("EHR") systems. Although reasonably precise with their readings, these corneal topographers are large, not portable, not typically useable in the standard exam room or "lane," and cost in the range of $12,000 to $50,000+, depending upon features. The combination of the size, the non-portability and/or the cost limits the prior corneal topography systems use and market reach.

In the case of Placido reflectance topography systems, each corneal device projects a specific illuminated source pattern to the eye being tested (typically a series of concentric illuminated rings) and captures an image of the ring reflections from the cornea. Each corneal topography system creates a unique data file from the captured rings image, for each eye studied. The data files are numeric representations allowing 3-D reconstruction of the corneal surface curvature based on of the locations of the ring edges, compared to a calibration reference surface. For the purpose of this discussion and within this specification, "power" may be used as a synonym for "curvature" consistent with common use and these terms may be used interchangeably throughout the specification. Different corneal topography systems may structure their data files differently. These data files may not be interchangeable; and are typically only stored on the corneal topography system performing the measurements, however derivative maps (axial power maps) may be stored on network drives or output to EHR systems. The underlying data files are generally not shared, are not stored on network drives, or output to EHR systems.

Placido-based corneal topography is described in detail in Klyce S D, Oshika T: Placido-based topography. In: Corneal Surgery: Theory, Technique, & Tissue. Part II. Testing and Measuring Corneal Function. 4th edition. Ed., F S Brightbill F S, McDonnell P J, Farjo A A, McGhee C N J, Serdarevic O N, Mosby Elsevier, New York, N.Y., 2009, pp 75-82, the disclosure of which is incorporated herein by reference.

In specific situations, it is advantageous to compare two different corneal topography examinations (or exams) on the same eye from different test dates. This kind of testing may be referred to as "difference mapping," and may identify very early topographic change consistent with early keratoconus and/or unexpected corneal topographic change after laser vision correction surgery. The latter condition has been referred to as "post-LASIK ectasia" or keratectasia. In order to generate a difference map, a provider typically directs a technician to sit at the console of the corneal topography device, select a patient to be studied, select the "difference mapping" subroutine, highlight dates of studies from which difference maps will be constructed, and generate the output in a specific "difference map" format. An example of a difference map is shown in FIG. 1, which illustrates output of a difference map subsystem according to the prior art.

In the topographic difference map shown in FIG. 1, green colors (the light areas in FIG. 1) map represent stable areas on a corneal surface (e.g., little or no topographical change). In FIG. 1, warmer colors (yellow and red which are represented by the "steeper" reference or legend in FIG. 1) on a difference map represent areas of the cornea that became steeper (higher in power), while cooler colors (blue and purple colors which are represented by the "flatter" reference or legend in FIG. 1) represent areas that became flatter (lower in power). Historically with these prior corneal topography systems, it has typically not been possible to create difference maps where topography studies on two different exam dates were performed by different corneal topography instruments. Therefore, even if other printouts such as power maps are available, they can't be used to construct difference maps as the underlying data files are not associated with these types of output. In other words, the underlying data files from the different corneal topography systems are not compatible with each other and cannot be compared with one another with commercially available software. A difference mapping process compares corresponding datapoints and associated measurements of the examined cornea from two selected studies on the different dates and does not compare the power maps (e.g., images). The datapoints are generated by analyzing the images captured by the corneal topography instruments. FIG. 1 shows topographic maps several months apart of a keratoconus patient. The images look similar, but with the difference map (right most panel), areas that become steeper and flatter are indicted by arrows or identifier. These herald progression of the keratoconus disease, which alerts the health care professional that treatment is needed.

FIGS. 2A and 2B show the corneal topography changes that occur after a treatment for presbyopia. The left panel is a pre-treatment examination, whittle the central panel is the corneal topography after 1 month and the right most panel is the corneal topography after 3 months. While the changes are subtle, difference maps (lower panels) show the changes produced by the presbyopia treatment are stable with time. The lighter regions in the fierce maps indicate areas of higher induced power on the corneal surface.

Difference mapping is also the best way to identify small, early topographic change. It is significantly better than visually comparing different corneal topography examinations separately, as shown in FIGS. 2A and 2B FIGS. 2A and 2B illustrate output of a prior art difference mapping system. In FIGS. 2A and 2B, there is a small increase in corneal power between Exam A and Exam B taken one month apart (B-A). In the third study, C, one month further on, the change remains the same (C-A). This patient would be followed in subsequent months to ensure a stable topography that does not lead to ectasia and a reduction in vision. These examples show the importance of difference mapping in early diagnosing of diseases associated with small early topographic change.

The influence of therapeutic options including UV corneal cross-linking ("CXL")—For decades, pathology states of the cornea such as keratoconus could not be stabilized or reversed with any therapy. During the period of roughly 1970 through about 2010, keratoconus was one of the leading causes of need for corneal transplant surgery worldwide. Patients with keratoconus required specialized care, fitting with custom rigid gas permeable contact lenses, and other measures before some ultimately required transplant care. This created significant direct costs in medical care, as well as indirect costs including lost educational opportunity, lost work, reduced earning potential, affliction with a sometimes visually disabling chronic condition, and often psychological consequences.

In 1998, a treatment method called UV Corneal Cross-Linking ("CXL") was introduced (Spoerl E, Huhle M, Seiler T. Induction of cross-links in corneal tissue. Exp. Eye Res. 1998 January; 66(1):97-103). This treatment involved application of a Riboflavin solution to the cornea and then treatment with ultra-violet ("UV") light. The photochemistry is nuanced, but the result is that corneal collagen and the inter-collagen matrix could be strengthened by this treatment. CXL has become commonplace in the European union and many parts of the world; in 2017 a form of this treatment received FDA approval for commercial use in the US.

The advent of CXL is now recognized as a vital step in treating early keratoconus to prevent progression of disease, and the potentially vision-threatening consequences thereof. The need for corneal transplant care has dropped precipitously in the population of keratoconus patients who have received CXL treatment. The collateral consequences of lost educational opportunity, lost work, reduced earning potential and other societal costs have also dropped noticeably.

It is increasingly recognized that CXL represents a very practical treatment strategy for KC, and possibly other corneal conditions. Pioneers in this field recognize that to be maximally effective, a strategy of early screening and early detection needs to be put in place. The role of a small, cost-effective topography system such as Delphi, that creates a global topography database, may be important in expanding screening opportunities and, in combination with cloud-based difference mapping, enabling early disease detection. In essence, the advent of a new treatment modality (CXL) stimulates the desire to have a broad-based topography screening methodology in place that is cost effective, simple, and easy to use.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

The patent or application file will contain two drawings in color (as well as black and white copies of the drawings. Copies of this patent or patent application publication with color drawing(s) will be provided by the Office upon request and payment of the necessary fee.

A better understanding of the features, advantages and principles of the present disclosure will be obtained by reference to the following detailed description that sets forth illustrative embodiments, and the accompanying drawings of which.

DETAILED DESCRIPTION

Figure 1:
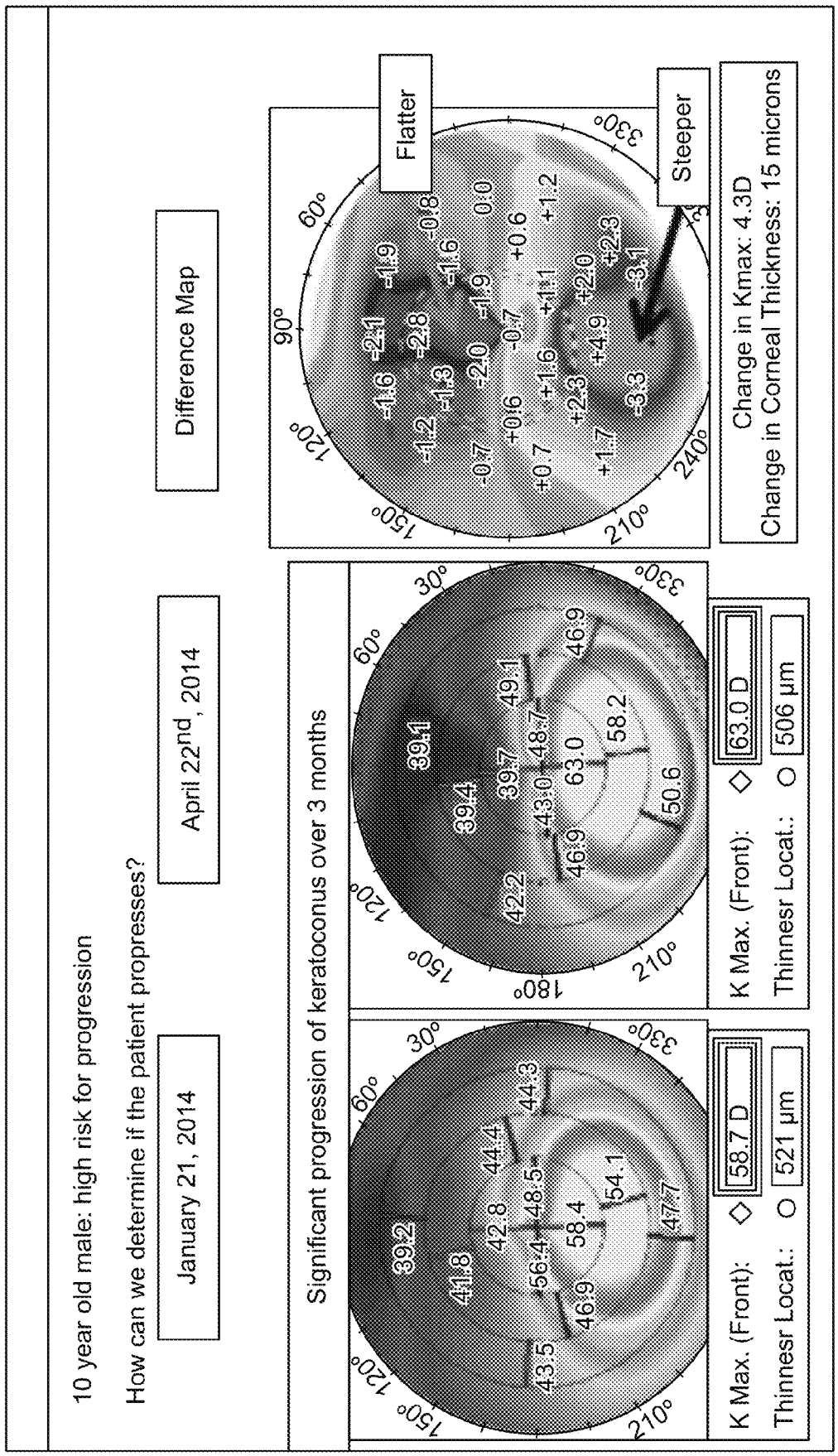
FIG. 1 illustrates output of a difference map subsystem according to the prior art.
Figure 2A:
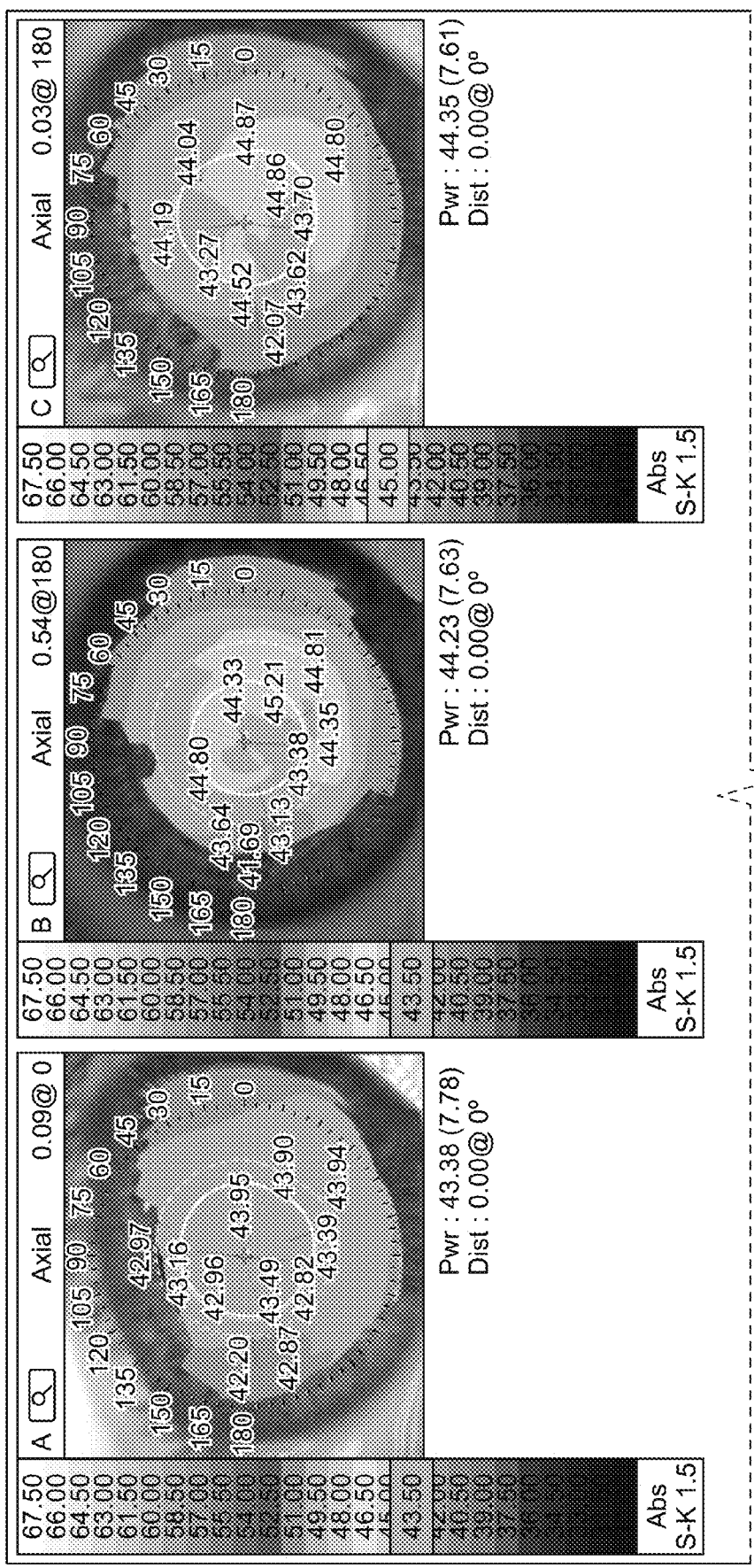
FIGS. 2A and 2B illustrate output of a prior art difference mapping system according to the prior art.
Figure 2B:
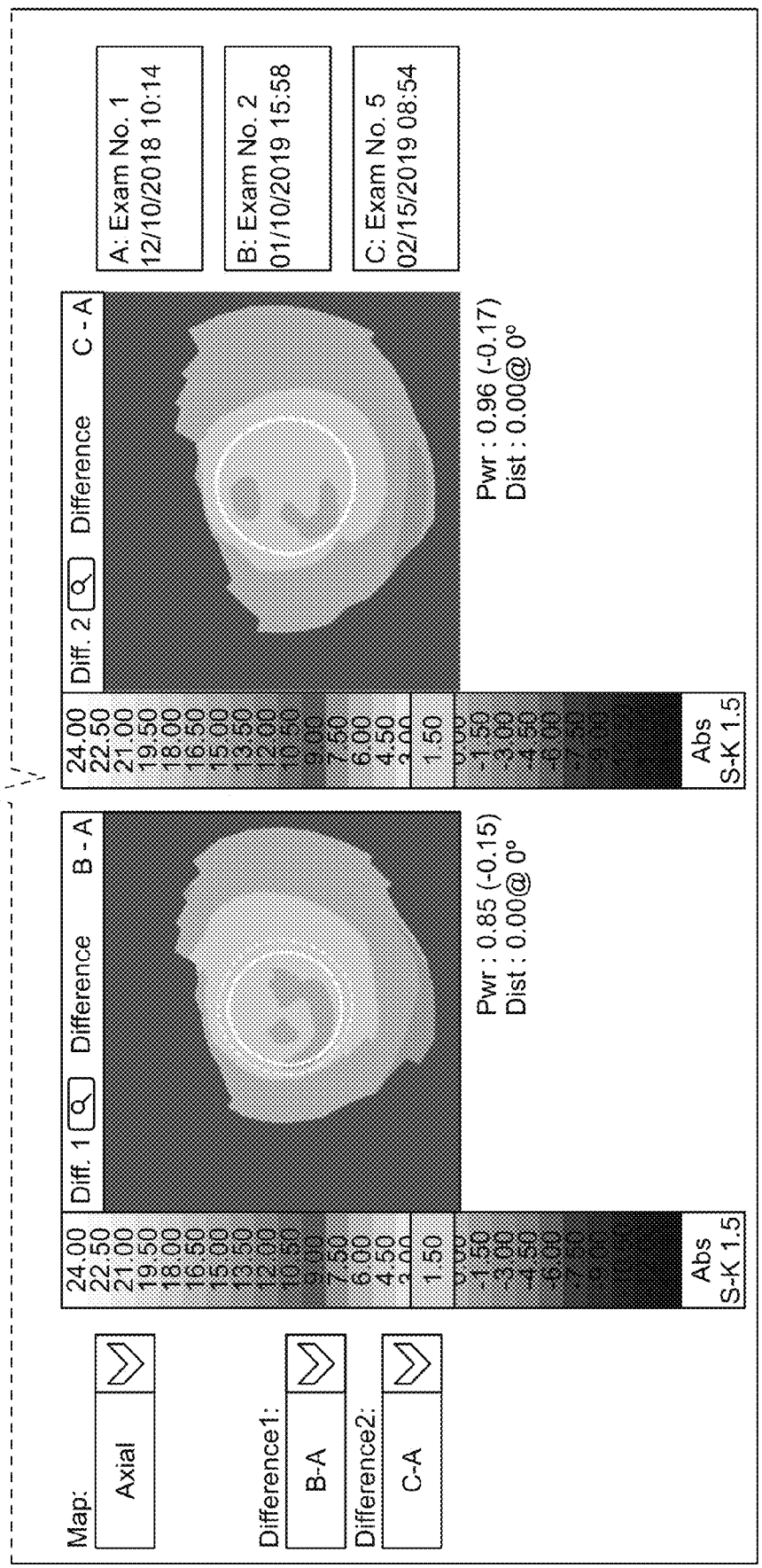

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

In some embodiments, the claimed subject matter may include difference-mapping computer-readable instructions stored in one or more memory devices. In some embodiments, the difference-mapping computer-readable instructions may be loaded into one or more volatile memory devices and may be executable by one or more processors of server computing devices that are located on the World Wide Web, the Internet or a global communications network. These server devices may be referred to as cloud-based server devices. In some embodiments, the difference mapping computer-readable instructions executable by the one or more processors on the cloud-based server devices may be referred to as cloud-based difference mapping ("CBDM") software. In some embodiments, a cloud-based difference mapping ("CBDM") system may include the cloud-based server devices that are running or executing the CBDM software.

As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The CBDM system may further store patient corneal diagnostic information, patient identification information and/or patient corneal datafiles in a database installed or resident on the cloud-based server devices. In other words, the CBDM system may also include one or more databases stored on the cloud-based server devices. These cloud-based server devices may be located in the same location or in many different locations. In some embodiments, medical providers may have accounts in the CBDM system where their patient records are stored in local cloud-based server devices. This database may be referred to as a provider corneal database or a provider database. In addition, the CBDM system may also link and/or associate with local databases in other cloud-based server devices located within a specific geographic area (e.g., within California, for example) to determine if other corneal topography studies have been performed on the patient. These databases may be referred to as local corneal databases or local databases. In some embodiments, the CBDM system may also link and/or associate with other databases in other cloud-based server devices within specific countries in order to allow the CBDM software to search and see if other corneal studies have been performed on the patient. In many cases, national or regional governmental and/or privacy regulations and/or considerations require patient information to be stored in cloud-based server devices that are physically located within the specific country and/or region. The linking and association of the local database to other databases within the specific county or region may be referred to as a national database. In addition, the CBDM may also link and/or be associated with other databases in cloud-based server devices throughout the world. The linking and association of the local database to the other databases throughout the world may be referred to as a global database. In other words, the global database is stored in one or more cloud-based server devices stored throughout the world.

The claimed subject matter and subject matter described herein focuses on the automation of and significant improvement to current corneal difference mapping. The CBDM system makes it possible to automate and significantly improve the corneal difference mapping process. In addition, the claimed subject matter described herein reduces the potential number of examiner errors. Further, it improves the process of notifying the examining provider and the patient (or parent/legal guardian) of potential corneal issues. In some embodiments, the CBDM software on the CBDM system may automatically perform difference mapping on two corneal topography studies if, for example, the examined patient has two studies separated by some established or threshold time interval (typically 6 to 12 months). Thus, in some embodiments, if there is any even slight topographic change consistent with a condition of concern, or a pathology state (e.g., a clinically relevant topography change), the CBDM software may electronically notify the medical provider (e.g., via email, text message, or other alerts). In some embodiments, after alerting the medical provider, the CBDM software may further notify the patient (or parent or legal guardian) via email or text message to a mobile communication device associated with this patient record.

An improved difference mapping process facilitates easier, automatic and earlier detection of pathology states such as keratoconus. This is significant to medical providers because treatment methods exist to stabilize corneal collagen, including corneal cross-linking ("CXL"), and an improved difference mapping process makes it possible to identify candidate patients for treatment sooner. Earlier detection and treatment can prevent many of the adverse consequences of later diagnosis, including significant topographic change with consequent optical degradation of the cornea resulting in visual loss. Prior to the advent of CXL therapy, keratoconus carried risk of significant lifestyle disruption, with loss of educational opportunity (missed days in school), lost work time, diminished earning potential, and need for specialized tertiary care from corneal specialists. This typically might include special testing, fitting with special contact lenses (now scleral rigid gas-permeable or "scleral RGP" lenses, formerly with hard plastic "PMMA" lenses) and occasionally might require surgical intervention including corneal transplant care.

In some embodiments, the Delphi corneal topography system is a small, portable corneal topographer that integrates a proprietary Placido disc illumination system and Keplerian telescope imaging optics with a dedicated smartphone or mobile communication device. In some embodiments, computer-readable instructions executable by one or more processors (e.g., a proprietary software application) 1) stores provider information, receives subject or patient information; 2) facilitates image capture; 3) finds the ring edges within the image; 4) constructs a data file of the ring edge locations according to a specific protocol; 5) Derives various types of corneal power maps for display on the mobile communication device display screen; and/or 6) transmits or communicates essential data including each unique "data file" and calibration reference data to a cloud server via secure, encrypted, HIPAA-compliant means; and 7) displays computer-generated interpretations or analyses of the study. In some embodiments, the Delphi corneal topography system may be offered to eye care professionals for a nominal cost plus an affordable monthly subscription fee, which is a unique pricing paradigm for essential diagnostic equipment in the healthcare industry. This revenue model may be attractive to eye care professionals globally, as it enables them to incorporate industry-leading technology into their care delivery processes without incurring significant upfront costs; matching equipment/service expenses to their revenue streams.

It is anticipated that this mobile communication device-based corneal topography system may facilitate the following: 1) Expansion of topography access to eye care professionals worldwide. Currently, commercially available computer-based corneal topography instruments are often prohibitively expensive for practitioners, particularly in smaller offices in urban or rural locations, or less economically privileged geographies worldwide. Providing high-quality systems at very low cost enables significant improvement in availability of diagnostic eye care for patients served by eye care professionals globally. 2) Exam room convenience and improved patient experience—The Delphi system (mobile communication device-based corneal topography system) is designed to attach to a slit lamp microscope, which is present in virtually every eye care practitioner's office worldwide. This concept enhances patient experience by minimizing their movement while allowing them to be examined in a familiar environment with a non-intimidating equipment that provides the examining physician rapid access to precise diagnostic data. By comparison, legacy topography devices are much larger, affixed to dedicated personal computers, and are mounted on motorized power tables that occupy a significant enough footprint. In offices that do have room to accommodate these larger systems, patients typically are first taken through separate testing rooms where these devices and others are located and are then taken into traditional exam rooms or "lanes" where the basic eye examination is performed. By making the device very small, smartphone (or mobile communication device)-based, and portable, the workflow is enhanced for the provider. 3. Cloud storage, telemedicine, and aggregate data analysis opportunity—In some embodiments, a cloud portal will allow provider access to studies of their patients which are retained in (HIPAA- and GDPR-compliant) cloud-based servers or remote computing devices. In some embodiments, medical providers may access their cloud data through login with unique account userID and password. In these embodiments, Delphi's cloud-based architecture may permit easy data access and sharing with eye care professionals (from any tablet, laptop or desktop computing device) who have account access. This access feature permits numerous telemedicine applications, allowing experts anywhere in the world the opportunity to review test data, enabling them to assist in the diagnostic process, or conduct research.

In U.S. patent application Ser. No. 16/447,642, filed Jun. 20, 2019, entitled "Use of Near Field Communications Technology to Transfer Patient-Related Data to Diagnostic Medical Equipment in a Medical Office or Other Healthcare Facility", a system and method for transmitting certain patient identifier information using near-field communications protocol and associated chipsets ("NFC") is detailed and/or described. In some embodiments, a patient may be invited to download a software application ("app") to their own smartphone (or mobile communication device), accept an end-user license agreement ("EULA") and then use the app for a variety of functions related to their eye care professional's office. In some embodiments, these functions included in the software app includes providing an office address, providing contact info, providing driving directions, providing appointment reminders and/or scheduling, detailing aftercare instructions and providing other medical-related information for the patient. In some embodiments, a module or portion of the software app may allow the patient to enter personal info to be conveyed to a diagnostic device such as the NFC-enabled Delphi mobile communication device-based corneal topography system. In some embodiments, by having the software application include contact information such as email address and mobile phone number, the software app may meet and/or address GDPR requirements that require any provider of cloud storage that stores personal info to have a system in place allowing any client (or patient) to request removal of information, or redaction of personal info from data collected.

Corneal topography systems evaluating the anterior surface of the cornea (e.g., like a Placido-reflectance system) generate data files including parameters or measurements of ring edge locations which represent these locations in polar coordinates through 360 degrees of arc, typically in 1 degree increments for all of the reflected Placido ring edges that can be identified in the captured rings image. Values for corneal power (axial, refractive, and tangential) and elevation are calculated by processor or processors within the Delphi unit and/or the mobile communication device for each found ring edge location and stored in the relevant data file for that examination. The data files also include calibration reference information and measurements along with patient diagnostic information. This patient diagnostic information includes right or left eye identifier data, exam time and date data, a topographer device identifier, a clinic and/or provider identifier, and exam alignment and quality data. This is not the patient identifier data which will be utilized by the CBDM software to locate prior patient corneal studies (which will be discussed below).

Corneal tomography systems evaluating the posterior surface and/or the anterior surface of the cornea acquire or generate elevation coordinates at multiple points on the corneal surface which are compared to points on a computer-generated best fit spherical or toroidal surface. In some embodiments, some devices utilize corneal tomography for the acquisition of spatial coordinates of multiple points from both the anterior and posterior corneal surfaces. In some embodiments, a device may utilize corneal topography to generate curvature coordinates on the anterior corneal surface and may utilize corneal tomography to generate elevation coordinates at multiple points on the posterior corneal surface.

In some embodiments, the cloud storage (e.g., the cloud-based server devices) of the CBDM system may create an opportunity to amass a large global topography database including patients from all over the world, with attendant research and data-mining opportunities, as discussed above and below. In these embodiments, these features may be compelling, both from a statistical analysis standpoint (being able to identify local, regional and possibly ethnic differences in pathology prevalence, hence risk) and from a "big data" perspective.

In some embodiments, a corneal topography system may have certain patient identifier information associated with each study. In some embodiments, this may, at a minimum, include a patient first name, a patient last name, and a date of birth, as well as a GPS location (or other geographic indicator) of the study. In addition, other patient identifier information may include a provider's EHR account number, contract information for the medical provider, and/or contact info for the patient including email address and/or mobile phone number. In some embodiments, other patient identifier information may include biometric information of the patient, e.g., fingerprints, voice files, facial feature data, and/or retinal scans. Any of the identifier information described above may be utilized alone and/or in combination with other identifier information in order to come up with a unique patient identifier (or unique ID). This unique ID may be utilized to determine if prior existing corneal studies exist for the patient in the databases of the CBDM system. Misspelling of patient names remains an issue in any storage of patient data which hinders searching for patients in any global database. Developing a unique ID for the patient helps address and alleviate this issue. Please note that the unique patient ID should not include any patient diagnostic or examination data.

In other words, the unique patient ID may allow the envisioned system to identify the same patient even if the patient has been studied at offices of two or more different (unrelated) provider offices, and/or has moved to a different geographic location (even if that different location is in another country). For example, if a patient has been studied at two different provider offices with the corneal topography system and data files have been stored in a database of the CBDM system, the CBDM software may search for the patient's identifier in one of the databases (e.g., the local database, the national database and/or the global database) and if a match is found with one or more of the patient's identifier, the CBDM software may be initiated and a difference map between the previous study and the most recent study may be performed and/or completed. In some embodiments, the CBDM software may communicate and/or alert the patient's computing device and/or the provider's (e.g., the most recent eye exam provider) computing device if necessary (e.g., if a clinically significant topographic change has been identified by the difference mapping process). In some embodiments, the CBDM software may allow and/or provide a global early-detection system that is larger than any provider office, network, or health-care system.

Figure 3:
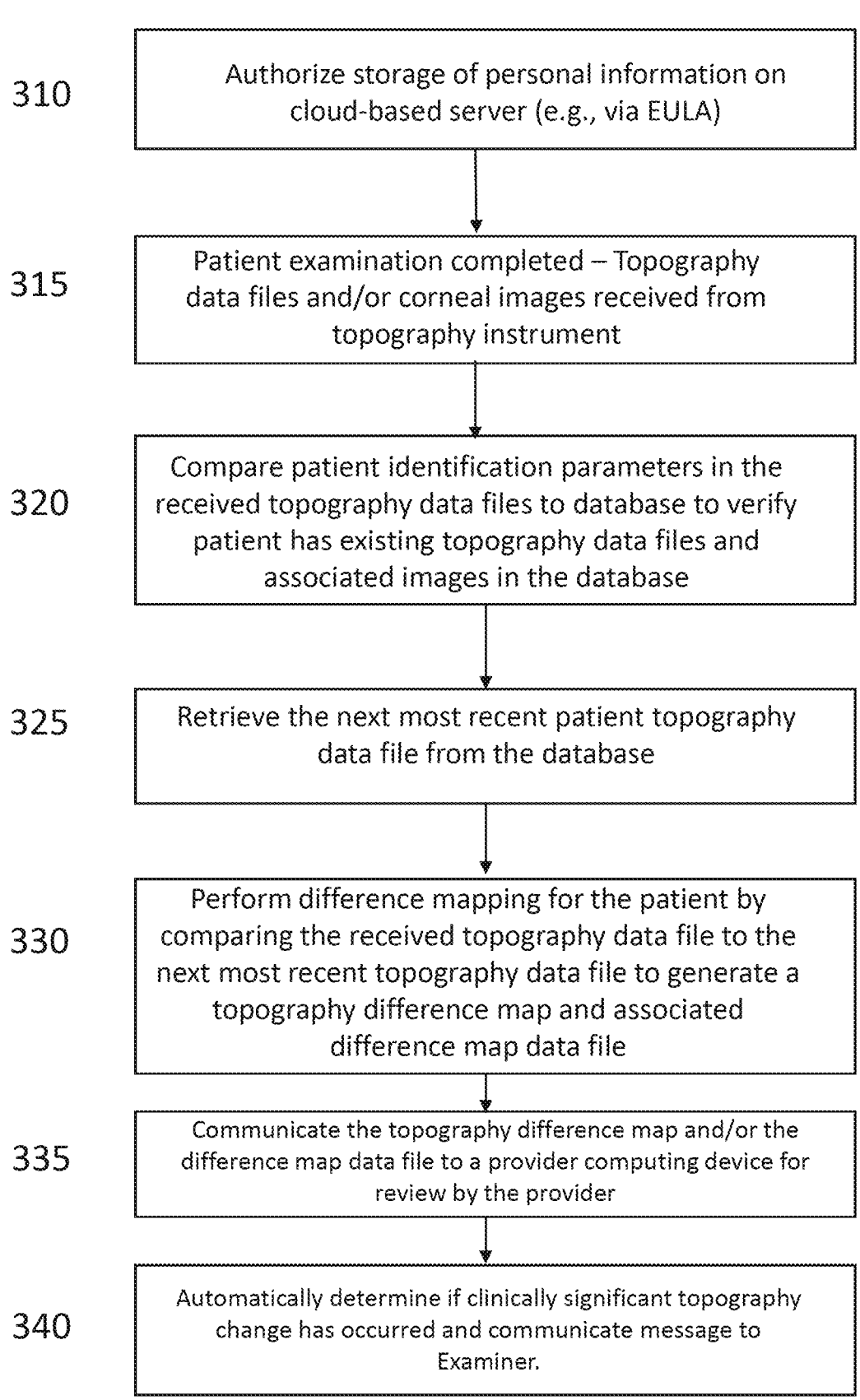
FIG. 3 illustrates a method of performing automatic difference mapping of corneal topography examinations according to some embodiments.

FIG. 3 illustrates a method of performing automatic difference mapping of corneal topography examinations according to some embodiments. A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein. The steps of the process listed below may be performed by the CBDM software.

In some embodiments, in step 310, a patient may authorize or facilitate collection of limited personal information to be used in association with storage of topography data files and/or corneal images in a database in the CBDM system. In some embodiments, a patient may have provided this authorization when downloading and/or operating a dedicated software application (e.g., by accepting an end user license agreement or EULA as described above).

In some embodiments, in step 315, a patient may have a corneal examination performed by a corneal topography system (e.g., a Delphi mobile communication device-based corneal topography system). In some embodiments, the corneal topography system may communicate one or more corneal topography data files and/or one or more corneal images. In some embodiments, the one or more topography data files may include reference data or measurements. In some embodiments, the one or more topography data files may also include time measurements (e.g., timestamps) to identify when the study was completed by the corneal topography system. In some embodiments, the data files and/or corneal images may be communicated for each eye of the patient. In some embodiments, the data files and/or corneal images for each eye may be communicated at the same time or at different times. In some embodiments, the topography data files and the corneal images may be transmitted at different times.

In some embodiments, in step 320, the CBDM software may automatically compare patient identification parameters in the received one or more topography data files to existing patient identification parameters stored in a database in the cloud-based server computing device to confirm and/or find that the patient has existing topography datafiles and/or associated studies in the database. In some embodiments, the CBDM software may first look in a provider database of the CBDM system. In some embodiments, the CBDM software may also look in a local database of the CBDM system. In some embodiments, the CBDM software may further look in a national database of the CBDM system. In some embodiments, in addition, the CBDM software may further look in the global database of the CBDM system. In some embodiments, the patient identification parameters may be a patient name, a numerical identifier, whether the data file is for a right eye or a left eye, a patient email address, and/or other identification parameters. In some embodiments, this just verifies that there is an existing datafile for the correct eye of the patient that is being examined. The examiner is not involved in making any of these determinations because the difference mapping software application may be programmed to automatically perform this confirmation and/or finding step. Thus, the use of the CBDM software application may eliminate any human or operator errors that may occur if different patient's studies were improperly selected and/or compared during the difference mapping process. This is a significant benefit of the CBDM application. In some embodiments, the CBDM software may be programmed to communicate with the cornea topography system if there are not existing topography data files for either eye or both eyes of the patient. Please note that the CBDM software being programmed or programmed to perform certain actions means that no operator or technician intervention is needed in order to perform these specific actions. In other words, the software executes this step (or steps) on its own after being initiated or initialized. The software also allows additional steps to be performed.

In some embodiments, in step 325, the CBDM software may be programmed to retrieve the patient's one or more most recent topography data files. In some embodiments, this may occur after CBDM software determines that the patient has existing studies in the database of the CBDM system. In some embodiments, this retrieved topography data file may be the data file to which the received current topography datafile will be compared.

In some embodiments, the CBDM software may be programmed to confirm that the topography data file being retrieved is for the correct eye. Again, the confirmation and/or the retrieval are initiated by the CBDM software and do not require any examiner or patient intervention. This also provides the advantage of eliminating operator error in retrieving the wrong topography data file by an operator selecting the wrong date (e.g., not the most recent topography data file for the patient), the wrong patient and/or in selecting the data file for the wrong eye.

In some embodiments, in step 330, the CBDM software may be programmed to perform difference mapping. In some embodiments, the received one or more topography data files (from the corneal topography device) may be automatically compared to the retrieved next most recent topography data file from one of the databases of the CBDM system. In some embodiments, the CBDM software may generate a difference map data file and/or a topography difference map image. In some embodiments, the CBDM software program may be programmed to be executed or performed for both eyes and their corresponding received topography data files (which are compared to the most recent study's topography data files for both eyes retrieved from the database of the CBDM system).

In some embodiments, an additional step may involve the CBDM software may be programmed to determine when the last topography examination of the patient was completed and then performing difference mapping against the last (or next most recent) topography data file if a date threshold has been met. In some embodiments, if the current date is Aug. 23, 2019, the most recent topography data file had a timestamp of Sep. 23, 2018, and the date threshold is 10 months from last examination in order to perform difference mapping, then the CBDM software may proceed with performing the automatic difference mapping. In some embodiments, the CBDM software may be programmed to include an option to display a list of all exams for a significant patient, so that a provider may select the exams to compare. For example, this may be helpful when repeat exams are performed in the same session owing to a technician or operator being challenged in obtaining a really good exam.

In some embodiments, the CBDM software may be programmed to generate a topography difference map data file and/or a topography difference map image. In some embodiments, the CBDM software may store the generated difference map data file and/or difference map image in the database (e.g., the provider database or a local database) in the CBDM system. In some embodiments, in step 335, the CBDM software may be programmed to communicate the generated difference map file and/or difference map image to a provider's mobile communication device (or a provider computing device). In some embodiments, there may be more than one difference map data files and/or difference map images communicated to the provider's mobile communication device. In some embodiments, difference map data file(s) and/or difference map image(s) may be communicated for each of the patient's eyes (e.g., the left eye and the right eye).

In some embodiments, in step 340, the CBDM software may be programmed to analyze the results of the difference mapping and determine that some clinically relevant topography change has occurred in the timeframe between the current examination and the most recent examination. In some embodiments, if a clinically relevant topography change has occurred, the CBDM software may automatically generate a message to notify the medical provider (e.g., via email, SMS text or other alerts to the medical provider computing device) of the clinically relevant topography change. In some embodiments, the CBDM software may automatically generate a message to notify the patient (e.g., via email, SMS text or other alerts to the patient computing device) of the clinically relevant topography change and may suggest a need for follow-up eye care. In some embodiments, the CBDM software may not communicate a message to the patient computing device unless the provider and/or patient has authorized that the message may be sent.

The above-identified process and/or method may be utilized for performing difference mapping for corneal topography systems that utilize an anterior corneal imaging device (e.g., a Delphi mobile communication device-based corneal topography system which utilizes reflectance Placido imaging), or a dual-surface corneal examination device (which evaluates and images both the anterior and posterior surface of the cornea). The data in the one or more data files of any of these corneal topography and/or tomography examination systems is a mathematical description of the examined patient's anterior corneal surface if a Placido-type reflectance system, and of both the anterior and posterior corneal surface if both are imaged by the corneal examination system. In some embodiments, each of the corneal imaging systems generate the associated corneal data for a left eye, a right eye and/or both eyes. Accordingly, corneal tomography datafiles may be compared by the CBDM system.

In some embodiments, the utilization of the regional, national and/or global databases in the CBDM system may provide additional advantages. For example, the CBDM system may identify patients that have changed eye care providers or moved to a new location and may perform difference mapping automatically in order to recognize potentially progressive eye conditions that appear to be worsening. In some embodiments, for example, if the CBDM software identifies that the current eye care professional does not have a previous eye study for the patient being examined (e.g. by checking the provider database), the CBDM software may automatically query a provider database, a local database, a national database, and/or a global database of topography data files generated by other corneal topography systems (having a compatible corneal topography software application as the corneal topography software application that generated the original patient study) in order to identify one or more existing topography data files for the patient. In some embodiments, the CBDM software then retrieve and utilize a most recent topography data file for the patient and automatically perform the difference mapping described above by comparing the received topography data file from the current examination and comparing it to the most recent topography data file retrieved from the provider database, local database, national database or global database.

In some embodiments, the CBDM software on the CBDM system may also evaluate whether a clinically relevant topographic change has occurred. In some embodiments, the CBDM software may also communicate a message via email or text message to the Provider's mobile communication device, or by posing a message in the Provider's cloud account portal to alert the medical provider that a prior topography data file exists, and that a clinically relevant topography change has occurred. In some embodiments, after first contacting or attempting to contact the provider, the CBDM software may also communicate a message to a patient's mobile communication device to alert the patient that a prior study was completed and that the difference mapping has identified possible clinically relevant topography change for which professional evaluation is advised. In some embodiments, the communication of the message to the patient may also occur via email, via text and/or any communication method the patient had originally provided when downloading the application to their mobile communication device allowing near-field communication conveyance of their personal identification information, accepting the End User License Agreement before first use, and thus giving the consent to the cloud server to store their personal information, contact information and/or corneal topography data files and/or images.

Figure 4:
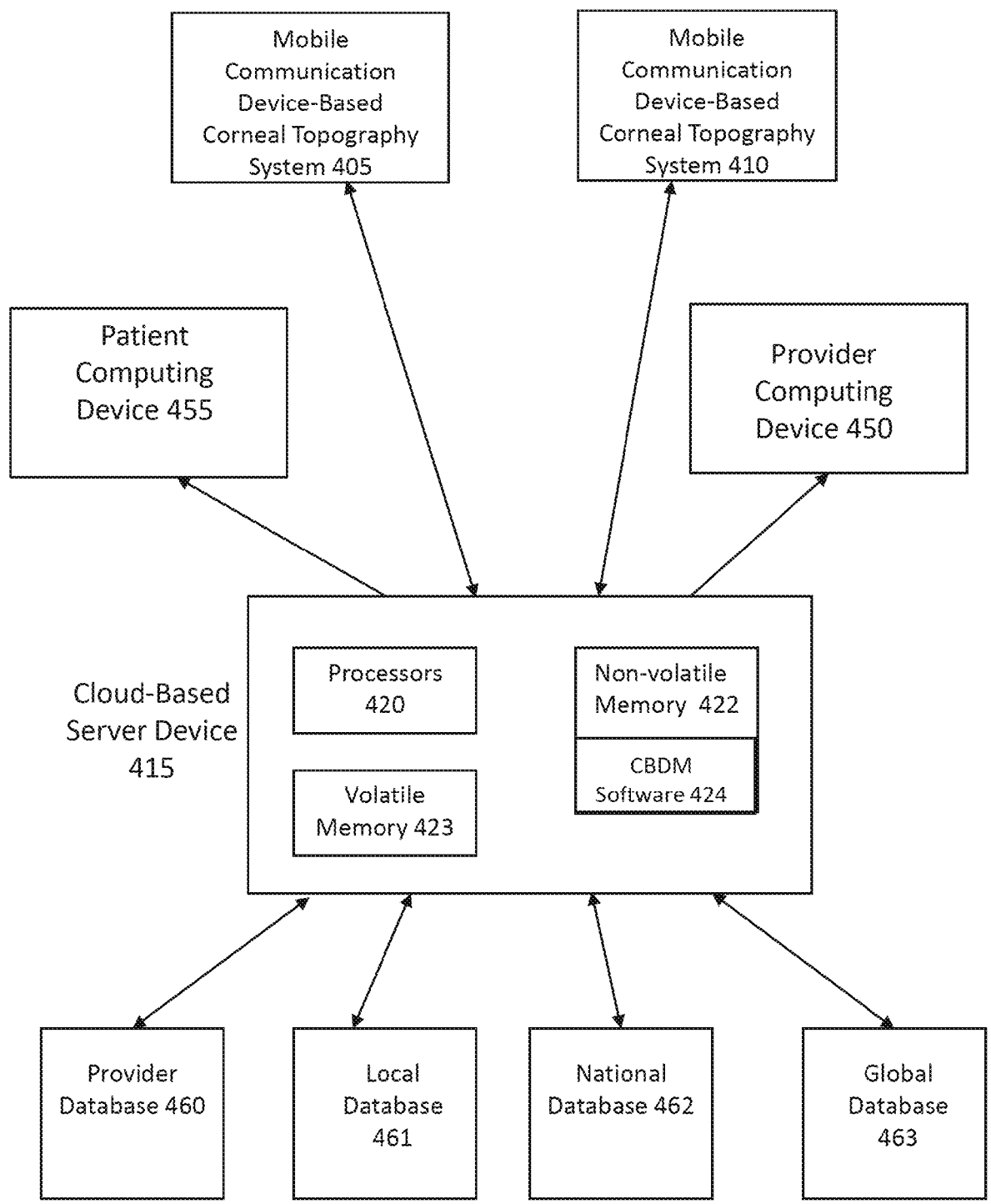
FIG. 4 illustrates a system including multiple corneal topography devices communicating with a cloud-based server computing device according to some embodiments.

FIG. 4 illustrates a system including multiple corneal topography devices communicating with the CBDM system according to some embodiments. In some embodiments, the CBDM system may comprise a first mobile communication device-based corneal topography system 405, a second mobile communication device-based corneal topography system 410 and/or one or more cloud-based server devices 415. In some embodiments, the one or more cloud-based server computing devices 415 may comprise one or more processors 420, one or more non-volatile memory devices 422, one or more volatile memory devices 423, the CBDM software 424 and/or one or more databases 460, 461 462, and/or 463. In some embodiments, the CBDM system may also comprise a provider computing device 450 and/or a patient computing device 455. In some embodiments, the first mobile communication device-based corneal topography system 405 and/or the second mobile communication device-based corneal topography system 410 may have operators perform corneal topography studies on patients. In some embodiments, either of the mobile communication device-based corneal topography systems may then communicate and/or transmit the generated one or more topography data files and/or associated images to the cloud-based server device 415. In some embodiments, the CBDM software 424 may be stored in one or more non-volatile memory devices 422. In some embodiments, the CBDM software may be loaded into the one or more volatile memory devices 423 and executed by the one or more processors 420. In some embodiments, the CBDM software 424 may communicate with the provider database 460, the local database 461, the national database 462 and/or the global database 463 to determine if the patient has had prior corneal examination studies performed. In some embodiments, if the CBDM software determines that a prior study exists, the CBDM software may communicate with the identified database (either 460, 461, 462 and/or 463) in order to retrieve the prior topography data files in order to perform difference mapping. In some embodiments, after the CBDM software 424 automatically performs difference mapping, the CBDM software 424 may communicate with the provider database 460 to store difference mapping topography data files and/or difference mapping images. In some embodiments, the CBDM software may communicate or transmit the generated difference mapping topography data files and/or difference mapping images to the provider computing device 450 for viewing and/or analysis by the medical provider. In some embodiments, the CBDM software 424 may also automatically determine if a clinically significant topographic change has occurred. If the CBDM software 424 makes this determination, the CBDM system may communicate a message to the provider computing device 450 identifying that a clinically significant topographic change has occurred and follow-up with the patient may be recommended. In some embodiments, the CBDM system may communicate a message to the patient computing device 455 to identify that a clinically significant topographic change has occurred, and that follow-up medical care may be recommended.

Figure 5A:
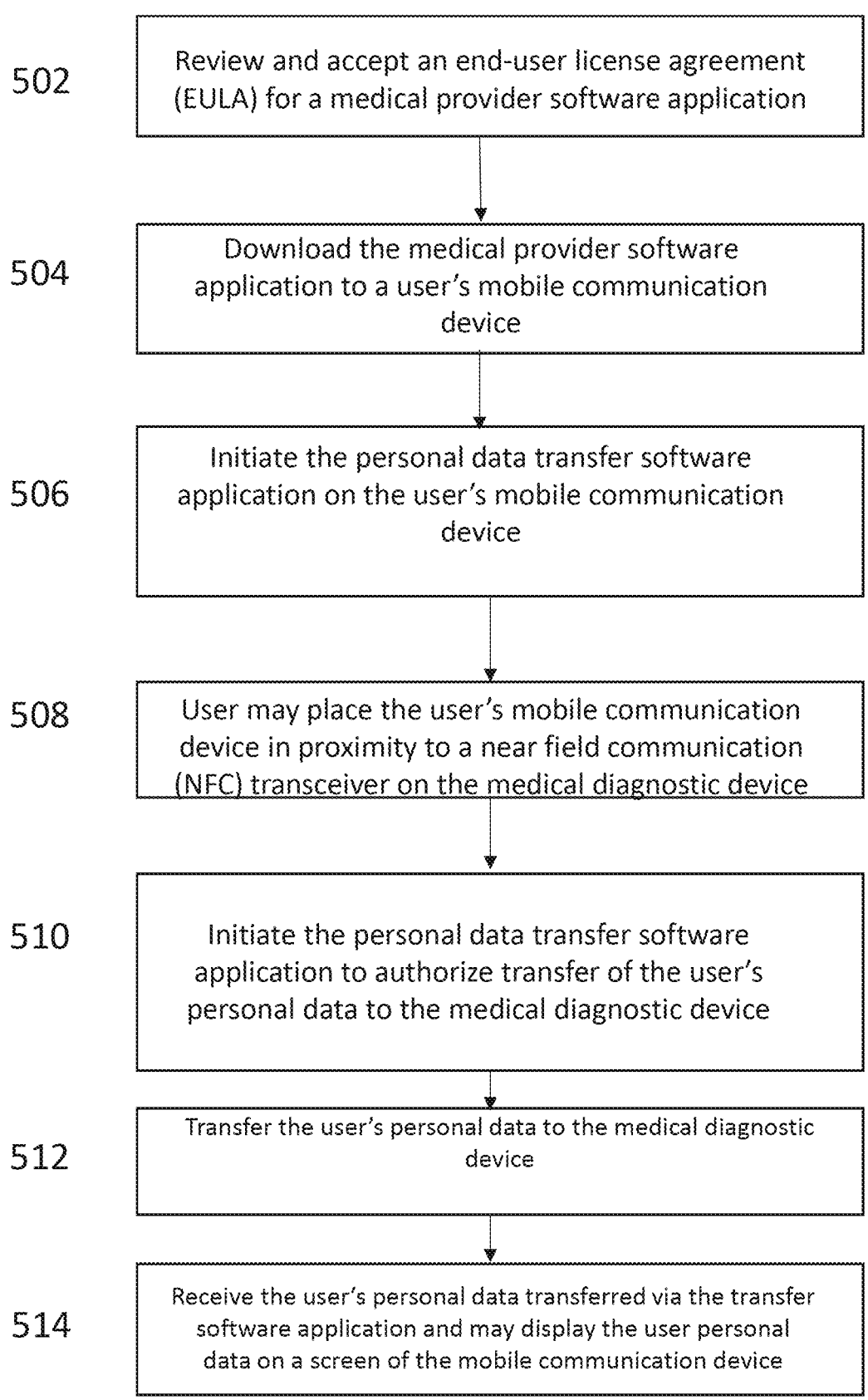
FIG. 5A illustrates a flow chart for creating a patient database according to some embodiments.
Figure 5B:
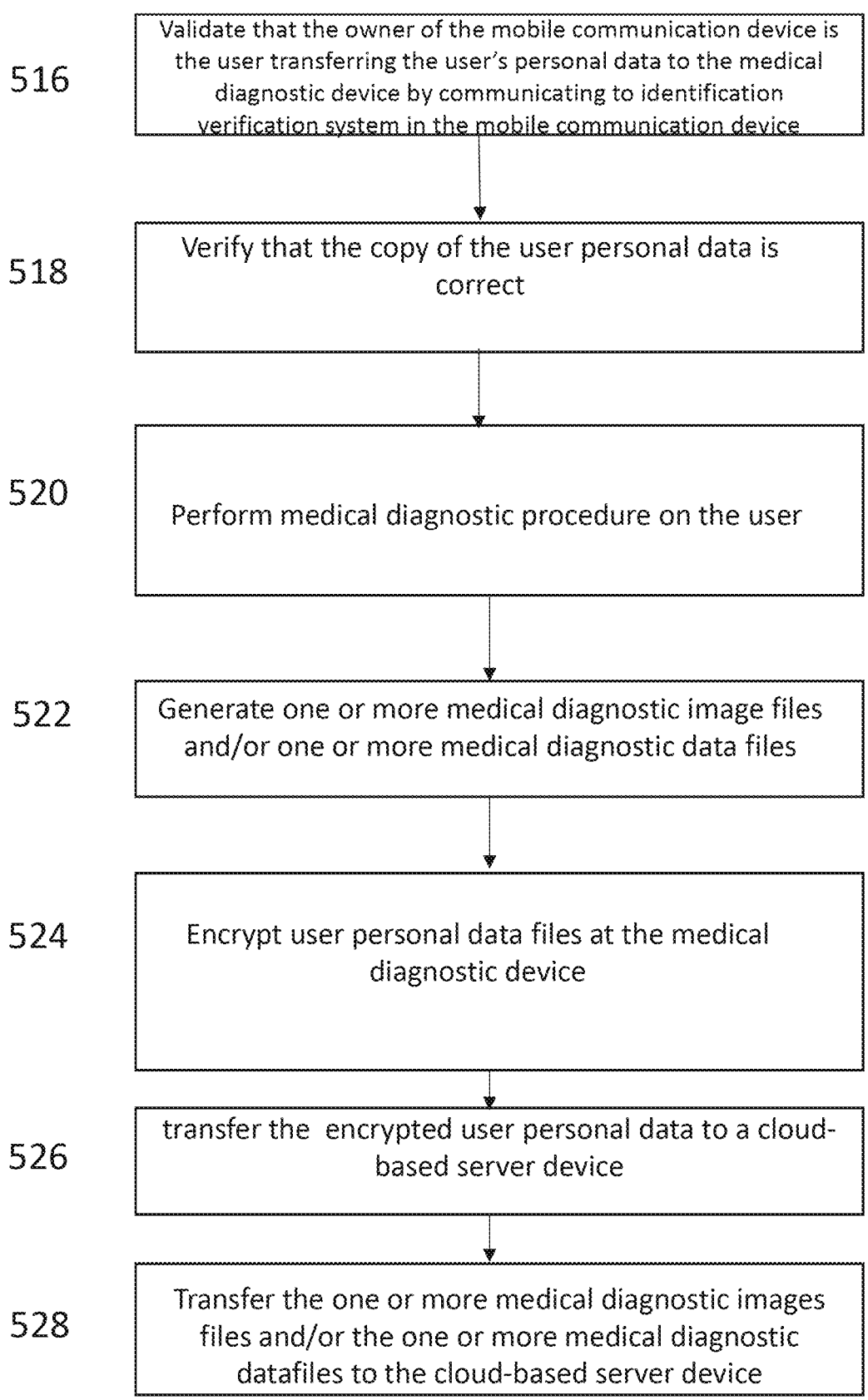
FIG. 5B illustrates a flow chart for creating a patient database according to some embodiments.
Figure 5C:
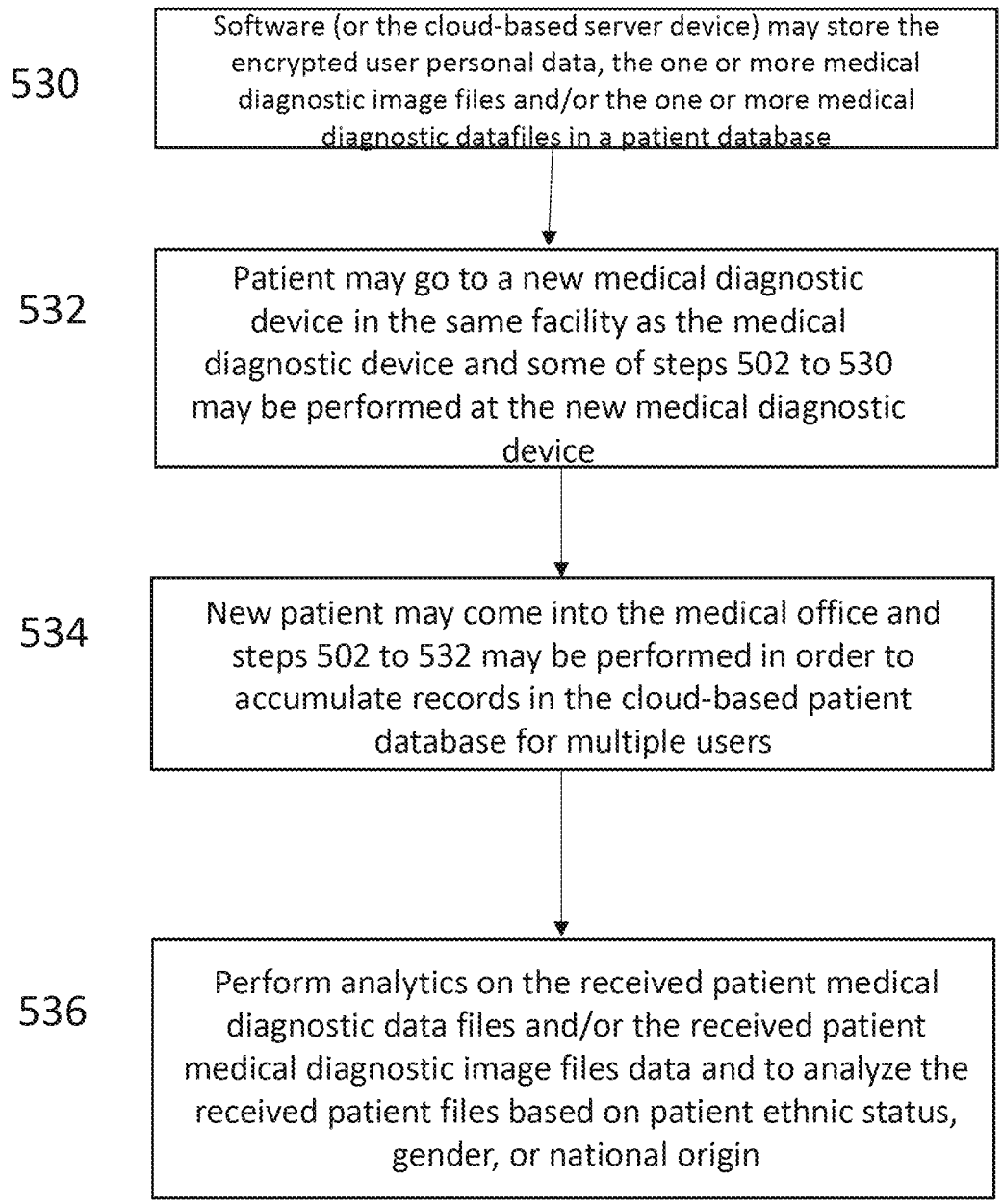
FIG. 5C illustrates a flow chart for creating a patient database according to some embodiments.

FIGS. 5A, 5B and 5C illustrate a flow chart for creating a patient database according to some embodiments. A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

In some embodiments, in step 502, a user may review and accept an end-user license agreement (EULA) for a medical provider software application. In some embodiments, the EULA may identify that the medical provider stores personal data of the user in the patient database and also stores user medical examination diagnostic data and images in the patient database. In some embodiments, in step 504, the user may download the medical provider software application to a user's mobile communication device, where the medical provider software application includes a personal data transfer software application. In some embodiments, the software application may receive a user's personal data and may store the user's personal data in a personal data transfer software application. In some embodiments, the user's personal data may include one or more of a user's first name, a user's surname, a user's cell phone number, a user's physical address, a user's email address, a contact method preference, and/or a user's date of birth. In some embodiments, the user's personal data may include user geolocation data and/or one or more of ethnic status, national origin, or gender data.

In some embodiments, in step 506, the user may initiate the personal data transfer software application on the user's mobile communication device. This may be initiated by selecting a button or icon and/or voice activation. In some embodiments, in step 508, a user may place the user's mobile communication device in proximity to a near field communication (NFC) transceiver on the medical diagnostic device. In some embodiments, the user may place the NFC transceiver in the user's mobile communication device over and/or next to the NFC transceiver in the medical diagnostic device. Specifically, in a mobile communication device-based corneal topography system, the NFC transceivers in the two mobile communications devices (the user's and the corneal topography system's) may need to be in close proximity in order for the data transfer to occur.

In some embodiments, in step 510, the software application, in response to user input to the user's mobile communication device, may initiate the personal data transfer software application to authorize transfer of the user's personal data to the medical diagnostic device. In some embodiments, in step 512, the software application may transfer the user's personal data to the medical diagnostic device. In some embodiments, in step 514, the software on the medical diagnostic device may receive the user's personal data transferred via the transfer software application and may display the user personal data on a screen of the mobile communication device so that the user may see the received data. In some embodiments, other computing devices may be utilized or the medical diagnostic device may have a computing device included and/or integrated therein and those displays may be utilized to display the user's personal data on a screen.

In some embodiments, in step 516, the software application may validate that the owner of the mobile communication device is the user transferring the user's personal data to the medical diagnostic device by communicating with an identification verification system in the mobile communication device. In some embodiments, the identification verification system may be FaceID, Touch ID or another biometric identification/validation system. In some embodiments, in step 518, the software application may verify that the copy of the user personal data is correct. In some embodiments, in step 520, a medical diagnostic procedure may be performed on the user.

In some embodiments, in step 522, the medical diagnostic device may generate (or the software application installed thereon) one or more medical diagnostic image files and/or one or more medical diagnostic data files. In some embodiments, in step 524, the user personal data files may be encrypted at the medical diagnostic device (or computing device utilized therewith). In some embodiments, in step 526, the medical diagnostic device (or computing device utilized therewith) may transfer the encrypted user personal data to a cloud-based server device. In some embodiments, the user personal data may not need to be encrypted but that may create a security risk. In some embodiments, in step 528, the medical diagnostic device (or computing device utilized therewith) may transfer the one or more medical diagnostic images files and/or the one or more medical diagnostic datafiles to the cloud-based server device. In some embodiments, this transmission of personal data, one or more medical diagnostic data files, and/or one or more medical diagnostic images files may be secure, encrypted and protected from outside third parties. In some cases, the transmission may be performed according to HIPAA guidelines. In some embodiments, in step 530, the software (or the cloud-based server device) may store the encrypted user personal data, the one or more medical diagnostic image files and/or the one or more medical diagnostic datafiles in a patient database of the cloud-based server device.

In some embodiments, in step 532, the user or patient may go to a new medical diagnostic device in the same facility as the medical diagnostic device and some of steps 502 to 530 may be performed at the new medical diagnostic device. This allows multiple medical diagnostic machines to be utilized with one patient during many visits. In some embodiments, the new medical diagnostic device may be within 200 feet of the first or original medical diagnostic device.

In some embodiments, in step 534, a new patient may come into the medical office and steps 502 to 532 may be performed in order to accumulate records in the cloud-based patient database. In some embodiments, the cloud-based patient database may be HIPAA compliant for some or all of the data and/or images stored therein.

In some embodiments, in step 536, computer-readable instructions that are executable by one or more processors of the cloud-based server device may perform analytics utilizing the patient personal data, the received patient medical diagnostic data files and/or the received patient medical diagnostic image files data and in some embodiments, may analyze the received patient medical diagnostic data files and/or patient medical diagnostic image files based on patient ethnic status, gender, or national origin. In some embodiments, the data may be analyzed according to other factors.

The patient and image data collected may be for a variety of medical diagnostic procedures and stored in one or more memory devices of the cloud-based server device. In some embodiments, the medical diagnostic device may be a corneal topography device, the one or more medical diagnostic image files may be corneal topography image files, and the one or more medical diagnostic datafiles may be corneal topography datafiles. In some embodiments, computer-readable instructions are executable by one or more processors of the cloud-based server device (the CBDM software) may perform difference mapping on the received corneal topography datafiles and a previous corneal topography datafile stored in the database. In some embodiments, the medical diagnostic device may be a corneal tomography device, the one or more medical diagnostic image files may be corneal tomography image files, and the one or more medical diagnostic datafiles may be corneal tomography datafiles. In some embodiments, computer-readable instructions are executable by one or more processors of the cloud-based server device (the CBDM software) may perform difference mapping on the received corneal tomography datafiles and a previous corneal tomography datafile stored in the database.

In some embodiments, the medical diagnostic device may be an autorefractor, the one or more medical diagnostic images files may include autorefractor image files and the one or more medical diagnostic datafiles may include corneal autorefractor data files. In some embodiments, computer-readable instructions may be executable by one or more processors of the cloud-based server device (the CBDM software) may perform difference mapping on the received autorefractor data files and a previous autorefractor data file stored in the database and retrieved therefrom.

In some embodiments, the medical diagnostic device may include wavefront sensors, the one or more medical diagnostic image files may include wavefront image files and the one or more medical diagnostic datafiles may include wavefront data files. In some embodiments, computer-readable instructions may be executable by one or more processors of the cloud-based server device (the CBDM software) may perform difference mapping on the received wave front sensor data files and a previous wavefront sensor data file stored in the database.

In some embodiments, the medical diagnostic device may include a fundus camera, the one or more medical diagnostic image files may include fundus image files and the one or more medical diagnostic datafiles may include fundus data files. In some embodiments, computer-readable instructions may be executable by one or more processors of the cloud-based server device (the CBDM software) may perform difference mapping on the received fundus data files and a previous fundus data file stored in the database.

In some embodiments, the medical diagnostic device may capture video of the user's cornea, the one or more medical diagnostic images files may be corneal video files and the one or more medical diagnostic data files may be corneal datafiles. In some embodiments, computer-readable instructions may be executable by one or more processors of the cloud-based server device (the CBDM software) may perform tear film break up time analysis by analyzing the received video of the user's cornea.

In some embodiments, the medical diagnostic device may capture images of a user's cornea and may generate corneal data files, may communicate the corneal images and the corneal data files to a database server. In some embodiments, the computer-readable instructions may be executable by one or more processors of the database server to perform ocular surface analysis based at least in part of the received corneal images and/or the corneal data files.

In some embodiments, a method to perform automatic corneal topography or tomography difference mapping may include computer-readable instructions stored in one or more memory devices of one or more cloud-based server devices. In some embodiments, the one or more processors in the one or more cloud-based server devices may be configured with the computer-readable instructions to receive one or more corneal topography or tomography data files and/or a corneal image for an examined patient from a corneal topography or tomography system; receive personal identification parameters from captured user personal data communicated from the corneal topography or tomography system; compare received patient identification parameters to existing patient identification parameters in a database to identify if there are existing topography or tomography data files for a same patient in the database; retrieve a prior topography or tomography data file for the patient from the database; and perform difference mapping by comparing the received topography or tomography data files to the prior topography or tomography data file retrieved from the database to generate a topography or tomography difference map. In some embodiments, the one or more processors in the one or more cloud-based server devices may be configured with the computer-readable instructions to: store the topography or tomography difference map in the database and associate the topography or tomography difference map with the user. In some embodiments, the one or more processors in the one or more cloud-based server devices may be configured with the computer-readable instructions to analyze the topography or tomography difference map to identify if a significant topographical change has occurred. In some embodiments, if the significant topographical change has occurred, the software may communicate the topography difference map and/or an advisory message associated with the topography or tomography difference map to a provider computing device for display to the provider. In some embodiments, the one or more processors in the one or more cloud-based server devices may be configured with the computer-readable instructions to analyze the generated topography or tomography difference map to identify if a significant topographical change has occurred. In some embodiments, if the significant topographical change has occurred, the one or more processors in the one or more cloud-based server devices may be configured with the computer-readable instructions to communicate an email or electronic message to a provider computing device. In some embodiments, the email or electronic message may include a link to the generated topography or tomography difference map stored in the database.

In some embodiments, the significant topographical change may be a change of 0.25 Diopters from the prior topography or tomography data file, and optionally may be within a change in the range of 0.20 to 0.30 Diopters from the prior topography or tomography data file. In some embodiments, the significant topographical change optionally may be within a change in the range of 0.10 to 0.40 Diopters from the prior topography or tomography data file. In some embodiments, the significant topographical change may be a change of 0.50 Diopters from the prior topography or tomography data file, or optionally may be within a change in the range of 0.40 to 0.60 Diopters from the prior topography or tomography data file. In some embodiments, the significant topographical change may optionally be within a change in the range of 0.25 to 0.75 Diopters from the prior topography or tomography data file. In some embodiments, the significant topographical change may be associated with early keratoconus, form frust keratoconus, changes in shape of cornea relating to Lasik, stability loss after refractive surgery, or eye rubbing in combination with a thin cornea.

In some embodiments, the one or more processors in the cloud-based server devices may be further configured with instructions to determine that the performing of the difference mapping is being completed on a correct eye of the patient by checking the personal information parameters that are associated with the datafiles. In some embodiments, the one or more processors in the cloud-based server devices further may be configured with instructions to compare current date of examination to prior date of examination for patient's existing topography or tomography data files to confirm a correct timeframe has elapsed to perform difference mapping. In some embodiments, the personal identification parameters may include a phone number, a first name and last name of patient, a date of birth and an email address of patient, and matching of any one of the personal identification parameters confirms a patient's record exists in the database.

In some embodiments, the one or more processors in the cloud-based server devices may further be configured with instructions to receive a patient thumbnail image communicated from the corneal topography or tomography system and compare the received patient thumbnail image to existing patient thumbnail images in a database to identify if there are existing topography or tomography data files for a same patient in the database. In some embodiments, the one or more processors in the cloud-based server devices may further be configured with instructions to receive a patient conjunctival capillary vessel architecture image communicated from the corneal topography or tomography system and may compare the received patient conjunctival capillary vessel architecture image to existing patient conjunctival capillary vessel architecture image in a database to identify if there are existing topography or tomography data files for a same patient in the database.

In some embodiments, a method to perform automatic corneal topography difference mapping may include computer-readable instructions stored in one or more memory devices of one or more cloud-based server devices. In some embodiments, the one or more processors in the one or more cloud-based server devices may be configured with the computer-readable instructions to: a) receive one or more corneal topography or tomography data files and/or a corneal image for an examined patient from a corneal topography or tomography system; b) may receive personal identification parameters from captured user personal data communicated from the corneal topography or tomography system and c) may compare received patient identification parameters to existing patient identification parameters in a database to identify if there are existing topography or tomography data files for a same patient in the database. In some embodiments, if there are no existing topography or tomography data files for the same patient in the database, the one or more processors in the one or more cloud-based server devices may be configured with computer-readable instructions to query a provider database, a regional database, a national database, a multi-nation database, and/or other foreign nation databases to determine if any of the databases include personal identification parameters matching the received personal identification parameters. In some embodiments, the one or more processors in the one or more cloud-based server devices may be configured with computer-readable instructions to communicate a message to a provider computing device requesting the provider to verify that the located personal identification parameters correspond to the patient being examined if the received personal identification parameters match personal identification parameters in the provider database, the regional database, the national database, the multi-nation database and/or the other foreign nation databases. In some embodiments, the one or more processors in the one or more cloud-based server devices may be further configured with computer-readable instructions to retrieve a prior data file for the patient from the database where the match was found for the received personal identification parameters; and perform difference mapping by comparing the received topography or tomography data files to the prior topography data file retrieved from the database where the match was found to generate a topography or tomography difference map. In some embodiments, the end-user license agreement (EULA) may authorize the medical provider or the database provider to transfer patient personal identification parameters and/or retrieved patient topography datafiles to the database provider if the patient has moved from one jurisdiction to another. In some embodiments, the EULA may authorize the database provider to directly contact the patient.

In some embodiments, an external validation process may verify that the person providing the personal data via near-field communication (NFC) is the mobile communication device that actually stores the personal data. Accordingly, before the personal data is transferred to the medical diagnostic device, the NFC transfer software application make an external communication or call to an identification (ID) verification system or subsystem already resident on the mobile communication device to verify and/or validate it is owner who is attempting to transfer the personal data stored in the phone. In some embodiments, after the ID verification system performs the verification, the PHI transfer application communicates the personal information via the NFC transceivers to the medical diagnostic device. In some implementations, such as with Apple mobile communication devices, the ID verification system may be either the Touch ID verification system or the Face ID verification system. In other mobile communication devices, other biometric ID verification systems may be utilized. In other mobile communication devices, other owner ID verification systems may be utilized that utilizes challenge words and/or user specific test questions.

First, in association with transfer of personal information by NFC, it may make sense to externally validate that the person sending is in fact the owner of the phone that is storing the information. Apple does this with Touch ID and Face ID and other phone manufacturers have similar systems. In some embodiments, the NFC app make an external call to an ID verification system already available on the phone that uses touch ID, Face ID, or similar owner identification before sending identifying information via NFC channels.

In some embodiments, it may be beneficial to provide a thumbnail image of the patient to the Examiner and/or the cloud-based difference mapping system to verify that a same subject is being examined by the testing apparatus. In some embodiments, the thumbnail patient image may be associated with the topography rings image. In some embodiments, a topography system or a mobile communication device-based topography system may capture and image of the patient's face as the patient is approaching the topography system. In some embodiments, the topography system may create a thumbnail patient image from the captured image. In some embodiments, the patient thumbnail image may be linked with the topography rings image and/or topography data files. In some embodiments, the patient thumbnail image may be communicated to the cloud-based server computing device. In some embodiments, an imaging device may be positioned within, located on, or partially enclosed on a side of the topography system that is facing the patient (e.g., by the eye cup and/or proximity sensors).

In some embodiments, the patient thumbnail image may be stored in a memory device of the cloud server computing device. In some embodiments, the difference mapping software executing on the cloud server computing device may compare the captured patient thumbnail image with a previously stored patient thumbnail image in order to verify that it is the same patient whose topographic data files are being compared. In other words, the patient thumbnail images from different dates may be compared against each other. In some embodiments, the Examiner may also view the patient thumbnail images in order to verify that the same patient is being examined and topographic image compared.

In some embodiments, the cloud-based server computing device may determine that the patient thumbnail images taken on different dates are not the same or are not consistent (e.g., it is potentially not the same individual), If the cloud-based server computing device determines that there is a discrepancy in the patient thumbnail image, the cloud-base server computing device may send an error message to the medical provider and/or may not perform difference mapping on the topography data files.

Second, there is probably some value to having a thumbnail photo of a subject's face associated with the topography rings image. In principle, this can be done by having one of the forward-facing cameras grab a facial image as the subject is approaching the front of the Delphi unit. Storage of thumbnail images in association with Placido reflectance rings images would enable an examiner (or possibly a cloud server system) to externally validate and confirm that the same subject is in front of the testing apparatus for topography study on a variety of different dates. Conversely, the system for topography study on a variety of different dates. Conversely, the system might identify the condition where in the face of the subject is not consistent between studies on different dates and this might send an error flag. Performance of corneal topography difference mapping in the cloud might potentially not be allowed if this condition is identified.

In some embodiments, an additional method for verifying that the same subject eye is being examined as the prior studies in the database may be the comparing of a patient's eye conjunctival capillary vessel architecture with the conjunctival capillary vessel architecture for studies stored in the patient database. This may be more accurate than utilizing a thumbnail image for comparison because the appearance of the anterior conjunctival vessels is consistent over decades (unless a patient has received surgical care rendered for pterygium or other conditions). Thus, a conjunctival capillary vessel architecture verification system could be utilized to verify that the two studies are being performed on the same eye of the same patient. A system that could capture the capillary vessel "map", that would allow comparison between studies taken on different dates, and would establish a separate verification and validation scheme that the same eye is being studied. This would be relevant since we anticipate performing difference mapping between two studies of the same eye of an individual subject on different dates.

In some embodiments, an imaging device in the corneal topography system may capture a conjunctival capillary vessel architecture image for the patient. In some embodiments, the corneal topography system may communicate the conjunctival capillary vessel architecture image with the topography datafiles and/or topography images to the cloud-based server computing device. In some embodiments, before difference mapping was performed between the topography datafile(s) received from the corneal topography system and the retrieved topography datafile(s) captured on different dates, the cloud-based server computing device would compare the conjunctival capillary vessel architecture image received from the corneal topography system with the conjunctival capillary vessel architecture images in the database from different examination dates to verify the same eye of the same patient is being examined. If the conjunctival capillary vessel architecture images were different, the cloud-based server computing device would generate an error message and/or would not perform difference mapping on the topography data files.

The one or more processor(s) as disclosed herein can be configured with instructions to perform any one or more steps of any method as disclosed herein. These may be computer-readable instructions that are executable by the one or more processor(s). As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor. The cloud-based server devices and/or remote computing devices may be one or more computing devices that are physically located at a geographic location away from the corneal topography systems (e.g., the Delphi mobile communication device-based corneal topography systems).

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation to determine a 3D process, use the result of the transformation to perform the 3D process, and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

As used herein, the term "or" is used inclusively to refer items in the alternative and in combination.

As used herein, characters such as numerals refer to like elements.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A method to perform automatic corneal topography difference mapping, comprising:
   computer-readable instructions stored in one or more memory devices of one or more cloud-based server devices;
   one or more processors in the one or more cloud-based server devices configured with the computer-readable instructions to:
   receive one or more corneal topography data files and/or a corneal image for an examined patient from a corneal topography system, the corneal topography system attached to a slit-lamp microscope;
   receive personal identification parameters from captured user personal data communicated from the corneal topography system;
   compare received patient identification parameters to existing patient identification parameters in a database to identify if there are existing topography data files for a same patient in the database;
   if there is no match between the received patient identification parameters for the examined patient and the existing patient identification parameters in the database;
   search a regional cloud-based corneal topography database by communicating a message to the regional cloud-based corneal topography database to determine if the regional cloud-based corneal topography database includes personal identification parameters matching the received personal identification parameters;
   communicate a message to provider computing device requesting the provider to verify that the additional personal identification parameters correspond to the examined patient in response to the received personal identification parameters matching the personal identification parameters in the regional cloud-based corneal topography database;

retrieve a prior corneal topography data file for the patient from the database or the regional cloud-based corneal topography database where the match was found for the received personal identification parameters; and perform corneal topography difference mapping in the cloud by comparing the received topography data foes to the prior corneal topography data file retrieved from the database or the regional cloud-based corneal topography database where the match was found;

utilize results of the comparison of the received corneal topography datafile to the prior corneal topography data file to generate a corneal topography difference map;

analyze the corneal topography difference map to identify if a significant topographical change has occurred, wherein the significant topographical change comprises a change of at least 0.25 Diopters from the prior corneal topography data file; and if the significant topographical change has occurred, communicate the corneal topography difference map and/or an advisory message associated with the corneal topography difference map to the provider computing device for display to the provider.

2. The method of claim 1, the one or more processors in the one or more cloud-based server devices configured with the computer-readable instructions to: store the corneal topography difference map in the database and associate the corneal topography difference map with the user.

3. The method of claim 1, the one or more processors in the one or more cloud-based server devices configured with the computer-readable instructions to:

communicate an email or electronic message to the provider computing device, the email or electronic message comprising a link to the generated corneal topography difference map stored in the database.

4. The method of claim 1, where the significant topographical change is within a range of 0.20 to 0.30 Diopters from the prior topography data file, and optionally within a range of 0.10 to 0.40 Diopters from the prior topography data file.

5. The method of claim 1, where the significant topographical change is a change of 0.50 Diopters from the prior topography data file, optionally within a range of 0.40 to 0.60 Diopters from the prior topography data file, and optionally within a range of 0.25 to 0.75 Diopters from the prior topography data file.

6. The method of claim 1, wherein the significant topographical change is associated with early keratoconus, form frust keratoconus, changes in shape of cornea relating to LASIK, stability loss after refractive surgery, or eye rubbing in combination with a thin cornea.

7. The method of claim 1, wherein the database is a HIPAA compliant database.

8. The method of claim 1, the one or more processors in the one or more cloud-based server devices further configured with instructions to:

determine that the performing of the difference mapping is being completed on a correct eye of the patient.

9. The method of claim 1, the one or more processors in the one or more cloud-based server devices further configured with instructions to:

compare current date of examination to prior date of examination for the prior corneal topography data file to confirm a correct timeframe has elapsed to perform the corneal topography difference mapping.

10. The method of claim 1, wherein the personal identification parameters include phone number, first name and last name of patient, date of birth and email address of patient, and matching of any one of the personal identification parameters confirms a patient's record exists in the database.

11. The method of claim 1, wherein an end-user license agreement (EULA) authorizes a medical provider or a database provider to transfer patient personal identification parameters and/or retrieved patient topography datafiles to the database provider if the patient has moved from one jurisdiction to another.

12. The method of claim 11, wherein the EULA authorizes the database provider to directly contact the patient.

* * * * *